April. 1, 1969 W. E. LAMMERTS Plant Pat. 2,876
ROSE PLANT
Filed July 28, 1967
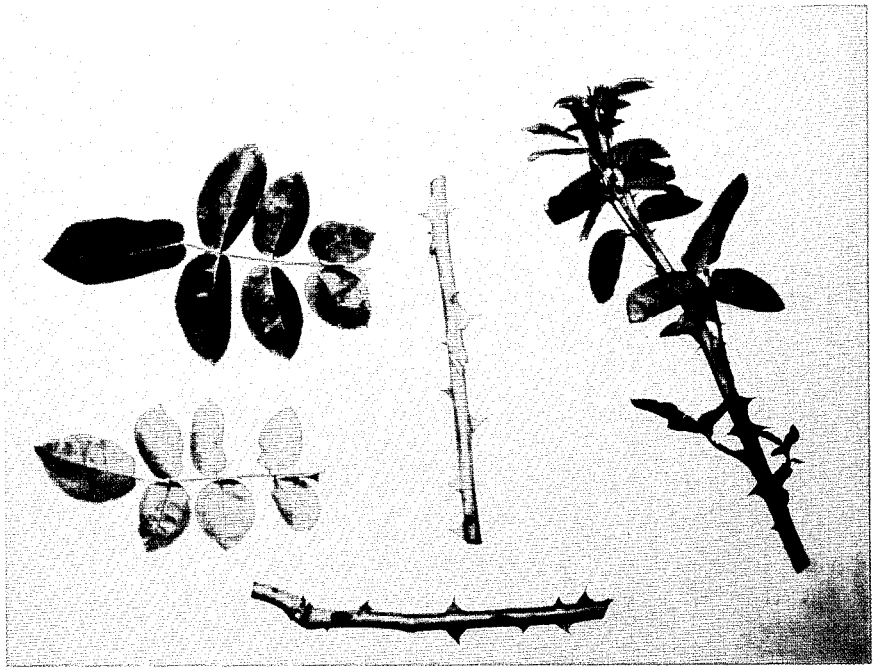
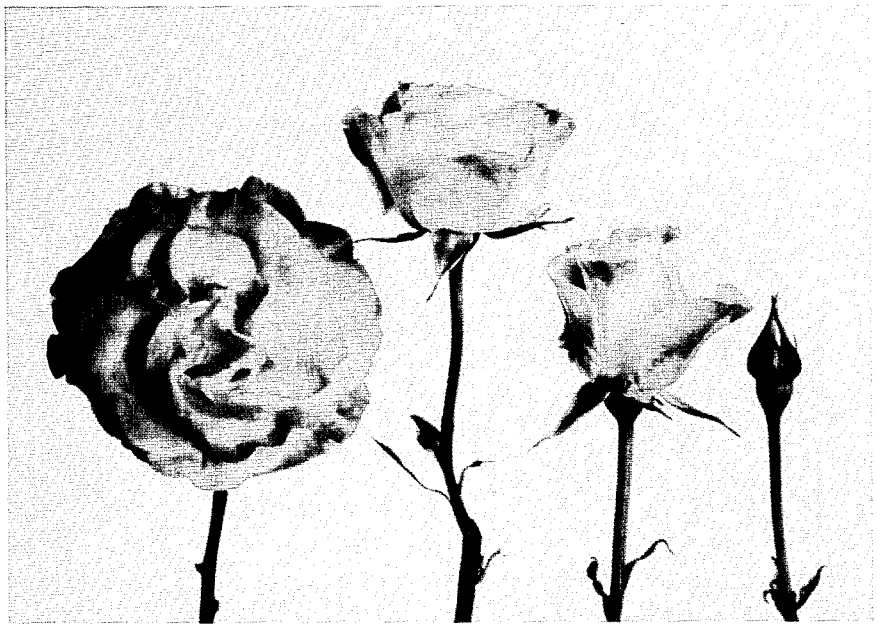
Inventor.
Walter E. Lammerts
By: Robbins Robb
Attorneys.

United States Patent Office

Plant Pat. 2,876

Patented Apr. 1, 1969

2,876

ROSE PLANT

Walter E. Lammerts, Freedom, Calif., assignor to Amling-De Vor Nurseries, Inc., Livermore, Calif., a corporation of California Filed July 28, 1967, Ser. No. 656,959

Int. Cl. A01h *5/02*

U.S. Cl. Plt.—11 1 Claim

The present invention relates to a new and distinct variety of rose plant of the hybrid grandiflora class, which was originated by me by crossing the rose variety known as "Queen Elizabeth" (Plant Patent No. 1,259) with the variety known as "Rumba" (Plant Patent No. 1,919).

As the result of this breeding, I have produced a new and improved rose variety which is distinguished from its parents, as well as from all other rose varieties of which I am aware, as evidenced by the following unique combination of characteristics which are outstanding therein:

(1) A well-defined grandiflora habit, with a bush height approximately the same as that of "Queen Elizabeth" and forming a moderately tall, well-shaped plant having upright and well-branched canes;

(2) Good adjustability to high-saline soils and good resistance to salt burn;

(3) Medium large, glossy, dark green foliage which is essentially disease resistant;

(4) Abundant bloom production from early spring to late fall, with the flowers usually borne in typical grandiflora clusters, but sometimes singly or in tighter clusters, on strong stems and necks;

(5) Urn-shaped buds which open to high-centered blooms at the half-open stage, said blooms being regular, well-imbricated, medium large in size and having good petalage when fully open, and the petals being unusually heavy, long-lasting, and very resistant to rain and weather injury, with the bloom tending to retain its crispness even through heavy rain downpours;

(6) A distinctive and attractive general color tonality of the flowers progressing from Canary Yellow in the bud and protected petals and Blood Red where the light first hits, to a gradual overall suffusion of Cardinal Rose, with the yellow pigment being much less intense and even sometimes appearing as ivory and the red color being also much less reduced under lower light intensities, while all colors tend to greatly improve and attain maximum development under conditions of bright sun and warm weather; and (7) A light spicy flower fragrance.

In comparison with its parent varieties, the new variety has largely inherited its striking flower color change, heavy petal substance and good petalage from the parent variety "Rumba," which bears small, bright yellow to red floribunda blooms in tight clusters on a moderately small, rounded bush having small, glossy foliage, while the greater bloom size, longer stems, vigorous and upright plant habit and larger foliage of the new variety are largely inherited from the parent "Queen Elizabeth," which is a vigorous, upright, pink-flowered grandiflora variety.

The new variety most nearly resembles the variety known as "Granada" (Plant Patent No. 2,214), which has a moderately spreading habit, with flowers having from 18 to 25 petals and ranging in color from lemon-yellow to nasturtium-red, but the new variety is easily distinguished therefrom by a more upright plant habit, a better imbricated bloom, a significantly greater petalage, heavier petals and a more intense color change of the flowers.

Asexual reproduction of my new variety by budding, as performed by me at Livermore, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the British Colour Council, except where general color terms of ordinary dictionary significance are obvious, as based upon observations of specimens grown at Shafter, Calif.

Type: Half hardy; tall, bush; outdoor; seedling; for cut flowers and mostly for garden decoration.

Class: Hybrid grandiflora.

Breeding: Seedling.

*Seed parent.*—"Queen Elizabeth."

*Pollen parent.*—"Rumba."

Propagation: Holds its distinguishing characteristics through succeeding propagations by budding.

*Flower*

Flowers borne: Singly and several to stem; in regular clusters; on stems of medium length.

Quantity of bloom: Abundant, outdoors.

Continuity: Continuous.

Fragrance: Slight. Nature—spicy.

Bud:

*Peduncle.*—Medium length; medium caliper; erect, rough; with numerous red hairs. Color—reddish.

*Before calyx breaks.*—Size—Medium. Form—oval; without foliaceous appendages on the surface of the bud; with entire foliaceous parts extending beyond the tip of the bud equal to ¼ or more of its length. Color—Erythrite Red, Plate 0027, with Cyprus Green, Plate 59.

*As calyx breaks.*—Color—no significant change.

*As first petal opens.*—Size—medium. Form—globular. Color: outside—Delft Rose, Plate 020; inside—Vermilion, Plate 18/3 to 18/2, with base of Canary Yellow, Plate 2.

*Opening.*—Opens up well.

Bloom:

*Size (when fully open).*—Medium; from 2½ inches to 4½ inches.

*Petalage.*—Very double; from 35 to 55 petals; arranged regularly.

*Form.*—High-centered at first and remaining high-centered; petals being at first rolled outward, but later becoming flat and rolled outward at maturity.

Petals:

*Texture.*—Thick.

*Appearance.*—Inside—satiny. Outside—satiny.

*Shape.*—Outside—round, with apex having one small point. Intermediate—round, with apex having one small point. Inside—oval, with apex having one notch.

This description of a newly opened flower was made from a rose grown outdoors during the month of June at Shafter, Calif.

*Color.*—Outer petal: outside surface—Delft Rose, Plate 020/1; inside surface—tip Blood Red, Plate 820/3, with center Porcelain Rose, Plate 620/3 and base Canary Yellow, Plate 2/1. Intermediate petal: outside surface—Begonia, Plate 619/1 and Canary Yellow, Plate 2/2; inside surface—tip Signal Red, Plate 719/3, with center Barium Yellow, Plate 503/1 and base Canary Yellow, Plate 2. Inner petal: outside surface—Canary Yellow, Plate 2/3 and Plate 2; inside surface—same as outside surface.

This description was made from a rose that was open for three days outdoors during the month of June at Shafter, Calif.

*Color.*—Outer petal: outside surface—Rose Opal, Plate 022/3 and white; inside surface—Cardinal Rose, Plate 822, Delft Rose, Plate 520/1, white and Canary Yellow, Plate 2/2. Inner petal: outside surface—Rose Opal, Plate 022 and white; inside surface—Orient Red, Plate 819/3 and white.

*General color effect.*—Newly opened flower—Blood Red and Canary Yellow. Three days open—Cardinal Rose.

*Behavior.*—Fading red; progresses to a more intense yellow and red color change.

*Flower longevity.*—On bush in garden—five or more days in June. Cut roses grown outdoors and kept at living-room temperatures—four days in June.

*Reproductive organs*

Stamens: Many; arranged regularly about pistils. Color—yellow.

Filaments: Medium length; most with anthers. Color—yellow.

Anthers: Medium size; all open at once. Color—yellow.

Pollen: Moderate quantity. Color—gold.

Pistils: Many.

Styles: Uneven; medium length; medium caliper; separated.

Stigma: Color—yellow.

Ovaries: All enclosed in calyx.

Hips: Ovoid; moderately smooth; walls thick and fleshy. Color—russet.

Sepals: Permanent; moderately long; straight; spear-shaped. Color—brown.

Seeds: Many; medium size.

*Plant*

Foliage:

*Leaves.*—Compound of five leaflets; abundant; medium large; moderately heavy; glossy.

*Leaflets.*—Shape—ovoid. Apex—mucronate. Margin—simply serrate.

*Color.*—Mature: upper surface—very dark green; under surface—light green. Young: upper surface—moderately green-bronze; under surface—light green-bronze.

*Rachis (the supporting stem of the compound leaf).*—Medium caliper. Upper side—smooth. Under side—moderately smooth.

*Stipules.*—Moderately short; moderately narrow; with medium long points turning out at an angle of less than 45°.

*Disease resistance.*—Good resistance to mildew and blackspot, as determined by comparison with other varieties grown under comparable cultural conditions at Shafter, Calif.

Growth:

*Habit.*—Upright; much-branched.

*Growth.*—Vigorous.

*Canes.*—Medium caliper.

*Main stems.*—Color—green-bronze. Thorns—several; medium length; straight; with long, narrow base. Prickles—none. Hairs—none.

*Branches.*—Color—green. Thorns—several; medium length; straight; with long, narrow base. Prickles—few; color—green. Hairs—none.

*New shoots.*—Color—green-red. Thorns—few; medium length; straight; with long, narrow base. Prickles—few; color—reddish. Hairs—none.

I claim:

1. A new and distinct variety of rose plant of the hybrid grandiflora class, substantially as herein shown and described, characterized particularly as to novelty by the unique combination of a well-defined grandiflora habit, with a bush height approximately the same as that of "Queen Elizabeth" and forming a moderately tall, well-shaped plant having upright and well-branched canes, good adjustability to high-saline soils and good resistance to salt burn, medium large, glossy, dark green foliage which is essentially disease resistant, abundant bloom production from early spring to late fall, with the flowers usually borne in typical grandiflora clusters, but sometimes singly or in tighter clusters, on strong stems and necks, urn-shaped buds which open to high-centered blooms at the half-open stage, said blooms being regular, well-imbricated, medium large in size and having good petalage when fully open, and the petals being unusually heavy, long-lasting, and very resistant to rain and weather injury, with the bloom tending to retain its crispness even through heavy rain downpours, a distinctive and attractive general color tonality of the flowers progressing from Canary Yellow in the bud and protected petals and Blood Red where the light first hits, to a gradual overall suffusion of Cardinal Rose, with the yellow pigment being much less intense and even sometimes appearing as ivory and the red color being also much less reduced under lower light intensities, while all colors tend to greatly improve and attain maximum development under conditions of bright sun and warm weather, and a light spicy flower fragrance.

No references cited.

ROBERT E. BAGWILL, *Primary Examiner.*